United States Patent
Busick et al.

(10) Patent No.: US 6,454,193 B1
(45) Date of Patent: *Sep. 24, 2002

(54) HIGH MASS TRANSFER ELECTROSPRAYER

(75) Inventors: David R. Busick, Lewis Center; James E. Dvorsky, Norwich Township; Gregory A. Trees, Columbus; James H. Saunders, Worthington, all of OH (US)

(73) Assignee: BattellePharma, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,541

(22) Filed: Apr. 20, 2000

Related U.S. Application Data

(60) Provisional application No. 60/130,873, filed on Apr. 23, 1999.

(51) Int. Cl.[7] ................................................. B05B 5/00
(52) U.S. Cl. ...................... 239/690; 239/3; 239/690.1; 239/692; 239/695; 239/696; 239/708
(58) Field of Search .......................... 239/3, 690, 690.1, 239/692, 695, 705, 706, 708, 696

(56) References Cited

U.S. PATENT DOCUMENTS

| | | | |
|---|---|---|---|
| 3,930,061 A | | 12/1975 | Scharfenberger |
| 4,383,767 A | | 5/1983 | Jido |
| 4,508,265 A | | 4/1985 | Jido |
| 4,581,675 A | * | 4/1986 | Kelly .......................... 239/704 |
| 4,765,539 A | | 8/1988 | Noakes et al. |
| 4,829,996 A | | 5/1989 | Noakes et al. |
| 5,813,614 A | * | 9/1998 | Coffee .......................... 239/690 |
| 6,302,331 B1 | * | 10/2001 | Dvorsky et al. ......... 239/690.1 |

* cited by examiner

*Primary Examiner*—Robin O. Evans
(74) *Attorney, Agent, or Firm*—Frost Brown Todd LLC

(57) ABSTRACT

A electrohydrodynamic aerosol sprayer wherein a gas flow deflector is used for creating a gas flow past the spray nozzle to stabilize the Taylor cone and to transport at least a portion of the aerosol away from the region downstream of the spray nozzle. This stabilization of the cone and transport of aerosol improves the droplet size and distribution and may also reduce the deposit of droplets on the internal components of the device.

16 Claims, 5 Drawing Sheets

HIGH MASS TRANSFER ELECTROSPRAYER

RELATED APPLICATION

This application claims priority from U.S. Provisional Application No. 60/130,873, filed Apr. 23, 1999.

BACKGROUND OF THE INVENTION

1. Field of the Invention

This invention relates to devices and methods for improving the delivery of aerosol spray in an electrohydrodynamic (EHD) sprayer.

2. Background

The use of electrohydrodynamic (EHD) apparatus to produce aerosols is well known. In typical EHD devices fluid delivery means deliver fluid to be aerosolized to a nozzle maintained at high electric potential. One type of nozzle used in EHD devices is a capillary tube that is capable of conducting electricity. An electric potential is placed on the capillary tube which charges the fluid contents such that as the fluid emerges from the tip or end of the capillary tube a so-called Taylor cone is formed. This cone shape results from a balance of the forces of electric charge on the fluid and the fluid's own surface tension. Desirably, the charge on the fluid overcomes the surface tension and at the tip of the Taylor cone, a thin jet of fluid forms and subsequently and rapidly separates a short distance beyond the tip into an aerosol. Studies have shown that this aerosol (often described as a soft cloud) has a fairly uniform droplet size and a high velocity leaving the tip but that it quickly decelerates to a very low velocity a short distance beyond the tip.

EHD sprayers produce charged droplets at the tip of the nozzle. Depending on the use, these charged droplets can be neutralized (with a reference or discharge electrode in the sprayer device) or not. The typical applications for an EHD sprayer without reference or discharge electrodes would be a paint sprayer or insecticide sprayer. Charged droplets in these types of sprayers may be preferred since the aerosol would be attracted to and tightly adhered to the surface being coated. However, with EHD apparatus used to deliver therapeutic aerosols, it is preferred that the aerosol be completely electrically neutralized prior to inhalation by the user to permit the aerosol to reach the pulmonary areas where the particular therapeutic formulation is most effective. Other drug delivery applications may dictate a small residual charge on the aerosol to accomplish some particular therapy.

During operation of the EHD device, the charged aerosol may leave the nozzle tip with very low velocity, and in the absence of some other force may build up in the region around the spray tip. This may be undesirable because the space charge on the aerosol may disturb the electric field and inhibit further aerosolization.

Another problem results from fluid wicking up the outside of the nozzle from the tip and either accumulating and/or flowing back to the tip where it may disrupt the Taylor cone. These disruptions and any other disruptions of the Taylor cone may result in a large variation in the size and size distribution of the aerosol droplets which is particularly undesirable in pulmonary drug delivery. A vertical orientation the nozzle reduces problems associated with the fluid collecting on or wicking up the outside of the capillary tube and associated fluid delivery means but it doesn't solve the problem.

When administering pharmaceuticals to a patient these limitations on orientation of the EHD apparatus result in either the patients having to tilt their head backwards or to lie on their back when the aerosol is delivered on axis with the nozzle. Alternatively, the EHD apparatus can deliver the aerosol vertically on axis with the nozzle and an elbow means can be used to change the direction of aerosol flow to deliver the aerosol more horizontally. With this change in direction of the aerosol, there often is an appreciable loss in the quantity of the aerosol. The loss in quantity is a result of the fluid impacting and depositing on the walls of the delivery device, particularly in the vicinity of the elbow, instead of reaching the patient.

Therefore, an EHD aerosol sprayer is needed wherein the Taylor cone can be stabilized to prevent disruption and wherein the aerosol may be swept away from the region near the spray tip and be delivered more efficiently to the device exit. Of particular need, is an EHD aerosol sprayer that can improve the mass transfer efficiency of the device and improve the aerosol droplet distribution.

SUMMARY OF THE INVENTION

In accordance with the needs and objectives, the invention is an EHD aerosol sprayer wherein the Taylor cone is stabilized to prevent disruption (often resulting in a narrower aerosol droplet size distribution) and wherein the aerosol is swept away from the region near the spray tip and delivered more efficiently to the device exit.

The EHD aerosol sprayer generally includes a spray nozzle having at least one spray tip near which an aerosolizable fluid exits the spray nozzle, forms a Taylor cone and is aerosolized by EHD spraying and a gas flow deflector for directing a gas past the spray tip to sweep the aerosol downstream and away from the spray tip to promote further aerosolization. Preferably the gas flow is laminar (typically slightly greater than aerosol velocity) to reduce turbulence near the Taylor cone. Typically, the gas deflector is such that it directs the gas along at least a portion of the spray nozzle and past the spray tip substantially completely around the spray nozzle. Typically, the Taylor cone is elongated away from the spray tip in a preferred direction and the gas flow deflector directs the gas past the spray tip substantially parallel to the preferred direction of the Taylor cone. Typically, the spray nozzle is elongated and the Taylor cone extends away from the spray tip parallel to the nozzle and the gas flow is therefore substantially parallel to the spray nozzle as it moves past the spray tip and the Taylor cone. The EHD sprayer may also include a discharge electrode for neutralizing the electric charge on the aerosol droplets and for creating a corona wind to both move the aerosol and create an induced gas flow past the spray tip. Multiple spray tips are typically utilized to deliver higher volumes of fluid.

The invention further includes a high mass transfer electrohydrodynamic aerosol sprayer comprising: a spray nozzle in fluid communication with a source of fluid to be aerosolized, the spray nozzle having at least one spray tip near which the fluid exits the spray nozzle, forms a Taylor cone and is aerosolized by electrohydrodynamic spraying; and a gas flow deflector for separating a gas flow into at least two portions, for directing a first portion of the gas past the spray tip to sweep at least a portion of the aerosol downstream from the spray tip and for further directing the second portion of the gas away from the spray tip but thereafter into contact with the first portion of the gas and the aerosol downstream of the spray tip.

Typically the spray nozzle has at least one spray tip near which the fluid exits the spray nozzle, forms a Taylor cone which is elongated away from the spray tip in a preferred direction and is aerosolized by electrohydrodynamic spraying and wherein the gas flow deflector is further capable of directing the first portion of the gas past the spray tip substantially parallel to the preferred direction of the Taylor cone. Preferably, the gas flow deflector directs the first portion of gas substantially completely around the spray nozzle and directs the second portion of gas substantially completely around the first portion of gas and the aerosol downstream of the spray tip. Generally, a plurality of spray nozzles and spray tips are utilized to produce additional quantities of aerosol.

In some cases, it is desirable if the gas flow deflector surrounds the spray tips and is designed such that the gas velocity is lower near the outlet end than near the inlet end. This may be accomplished where the cross sectional area available for the gas flow near the inlet of the deflector is less than the cross sectional area near the outlet end. It is also desirable in some cases where the volume and/or flow rate of the first portion is less than the volume and/or flow rate of the second portion. A particularly useful EHD sprayer employing the corona wind to provide induced airflow comprises a spray nozzle in fluid communication with a source of fluid and having at least one spray tip near which the fluid exits the spray nozzle, forms a Taylor cone and is aerosolized by EHD spraying along a path parallel to a selected aerosol spray direction; a discharge electrode for producing ions near an ionized site on the discharge electrode and a corona wind from the ionization site along a desired path and being oriented such that the corona wind causes a flow of gas past the spray tip and sweeping at least a portion of the aerosol away from the spray tip; a reference electrode located between the spray nozzle and the discharge electrode; a first voltage source maintaining the spray nozzle at a negative potential relative to the potential of the reference electrode; and a second voltage source maintaining the discharge electrode at a positive potential relative to the potential of the reference electrode. A preferred sprayer typically has the discharge electrode oriented such that the desired path makes an angle of less than 90 degrees to the selected aerosol spray direction. The device may also include a second reference electrode located such that the discharge electrode is located between the first reference electrode and the second reference and a third reference electrode located such that the spray nozzle is located between the first reference electrode and the third reference electrode. The reference electrodes typically are at potentials that are positive with respect to the spray nozzle and negative with respect to the discharge electrode.

The invention further includes a method of producing and delivering an aerosol to a desired site by aerosolizing a fluid from a spray tip by electrohydrodynamic spraying; separating a gas into at least two portions, directing a first portion of the gas past the spray tip to sweep at least a portion of the aerosol downstream from the spray tip, directing the second portion of the gas away from the spray tip, and contacting the second portion of gas with the first portion of the gas and the aerosol downstream of the spray tip and sweeping the aerosol to the desired site. The method typically includes aerosolizing the fluid from a Taylor cone which is elongated in a preferred direction away from the spray tip at one end of an elongated spray nozzle, and directing the first portion of the gas past the spray tip substantially parallel to the preferred direction of the Taylor cone. Generally, the method may be used with a plurality of spray sites to increase the mass of aerosol.

Preferably the method includes directing the first portion of gas substantially completely around the spray tip and directing the second portion of gas substantially completely around the first portion of gas and the aerosol downstream of the spray tip to provide a sheath of gas around the aerosol to protect it from deposit on the device surfaces.

The deflector may be designed such that the first portion of the gas directed past the spray tips is less volume than the second portion of gas directed away from the spray tips. The ratio of the first to the second portions may be used to control the aerosolization and the delivery of the aerosol. The velocity of the first portion of gas may also be controlled by the flow resistance. A deflector that has an increasing cross section in the downstream direction will have the effect of reducing the velocity of the first portion of gas. This may be desirable in some situations to further stabilize the Taylor cone. The method is particularly useful in a pulmonary delivery device where the aerosol is generated by EHD.

DESCRIPTION OF THE PREFERRED EMBODIMENTS

Figure 1:
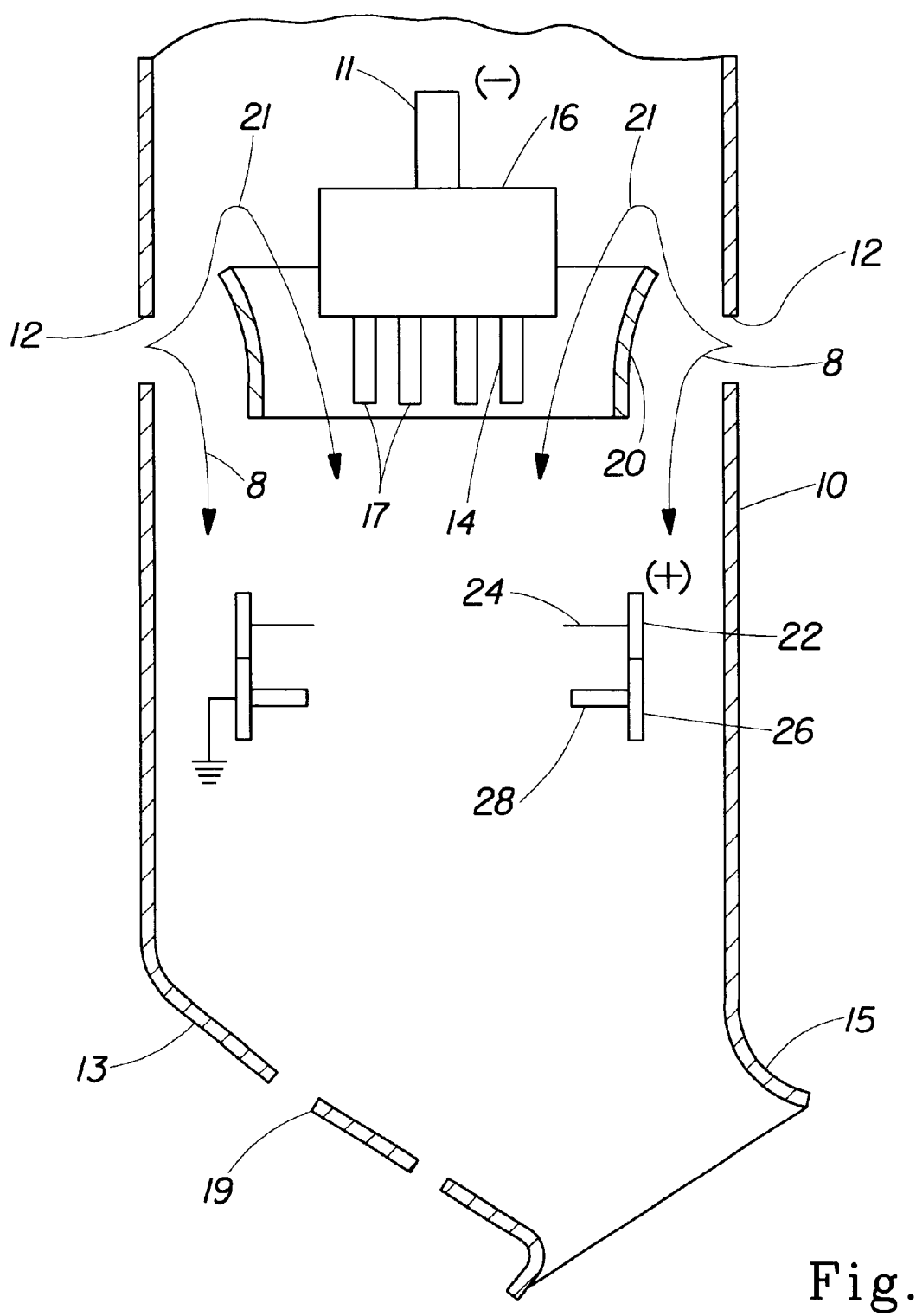
FIG. 1 is a cutaway view of an EHD sprayer according to the invention.

In EHD spraying, an aerosolizable fluid is delivered to a nozzle maintained at high electric potential. One type of nozzle used in EHD devices is a capillary tube that is capable of conducting electricity. An electric potential is placed on the capillary tube which charges the fluid contents such that as the fluid emerges from the tip or end of the capillary tube a so-called Taylor cone is formed. This cone shape results from a balance of the forces of electric charge on the fluid and the fluid's own surface tension. Desirably, the charge on the fluid overcomes the surface tension and at the tip of the Taylor cone, a thin jet of fluid forms and subsequently and rapidly separates a short distance beyond the tip into an aerosol. This aerosol has a fairly uniform droplet size and a high velocity leaving the tip but that quickly decelerates to a very low velocity a short distance beyond the tip. In the absence of some other force (other than the electrical repulsion), the aerosol may build up in the region just downstream of the spray tip. This build up may result in an electrical force back on the Taylor cone and/or a reduction in the electric field surrounding the Taylor cone. These effects may destabilize the Taylor cone and inhibit further efficient aerosolization. In particular, this destabilization may increase the size and broaden the size distribution of droplets in the aerosol. For some applications like pulmonary drug delivery, a broader size distribution can greatly decrease the efficacy of the therapy.

Another potentially destabilizing occurrence during EHD spraying is a phenomenon known as wicking on the spray nozzle. As fluid is dispensed from the nozzle to the Taylor cone at the spray tip it may collect on or wick up the outside of the nozzle and associated fluid delivery means. If the fluid flows up the outside of the nozzle from the tip, it is no longer available to be sprayed and represents a loss in efficiency of the device. Moreover, fluid on the outside surfaces of the capillary tube may accumulate and suddenly flow back to the tip where it may disrupt the Taylor cone again resulting in a large variation in the size and size distribution of the aerosol droplets.

Yet another source of inefficiency in EHD devices results from the depositing of aerosol droplets on the internal components of the device during the aerosol path from the spray tip to the exit of the device. Deposit of droplets is reduced if electrical charges on the droplets are discharged. However, any device components in the droplet path can still be sites for deposit. Any deposited droplets are generally lost. In some applications, upon impact with internal components the droplets could aggregate and form larger droplets that might either deposit or be re-entrained and delivered to the exit. Either way, the larger droplets may be fairly useless for some applications. In hand held pulmonary delivery devices, a particularly difficult component (as far as droplet deposit is concerned) is an elbow at the exit of the device which aims to turn a vertically oriented aerosol flow from the spray nozzle of the device into a horizontally delivered dosage to the user's mouth.

These problems in EHD devices may be reduced according to the invention by providing a flow of gas near the spray nozzle and spray tip. By controlling this gas flow we have found that 1) the Taylor cone is stabilized, 2) that any fluid which attempts to wick to the outside surface of the spray nozzle is pushed back into the Taylor cone by this gas flow, 3) that the electrical field or space charge around the Taylor cone is reduced or eliminated by sweeping away the aerosolized particles downstream of the spray tip, and 4) that in a preferred embodiment, gas flow entirely around the spray tip can form a protective sheath around the aerosol along its flow path through the device to the exit while substantially reducing the deposition of droplets on the device walls and internal device components (such as an elbow) in the path to substantially increase mass transfer through the device.

Figure 2:
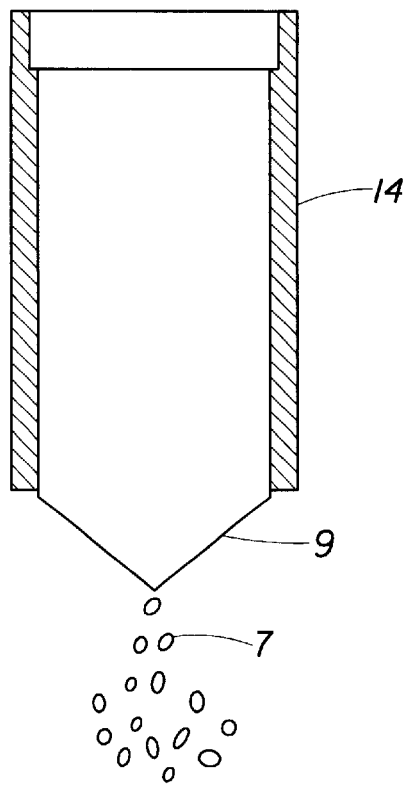
FIG. 2 is a view of the spray nozzle and Taylor cone of the EHD spray device shown in FIG. 1.

One embodiment is shown in FIGS. 1 and 2. This embodiment could, for example, be used in a hand held EHD device for pulmonary drug delivery. A housing includes an exit opening 15. For pulmonary drug delivery, exit 15 could, for example, directly contact a user's mouth or connect to a face mask or other interface leading to the user's mouth. As shown, slanting wall or elbow 13 is used to change the direction of an aerosol from essentially vertical to more horizontal for ease of delivery to an upright user. The housing may contain optional air holes 12 and/or 19 for entry of any air needed during an inhalation cycle, for example. Clearly, the higher the ratio of air through optional holes 12 to that through optional holes 19, the greater the flow past the spray nozzles. Alternatively, a source of air or other gas could be provided within the device in the region near the air holes upstream of the location where the aerosol is produced. The source of gas could, for example, be from a pressurized container, a mechanical device such as a bellows or other common source. The wall 13 may contain optional air holes for additional air flow and to keep droplets off the wall.

The EHD device includes fluid delivery means including a connector 11 to a source of fluid to be aerosolized and optional manifold 16. The fluid is delivered to spray nozzles 14. Spray nozzles 14 may be any means for delivery of the fluid for producing a Taylor cone 9 at a spray end or tip 17 of the nozzle, such is well known within the electrospraying art. A voltage source is applied to the spray nozzles to produce a high electric field around the spray tip. In FIG. 1, the charge on the spray nozzle is shown as negative, but a positive charge would also be useful. When the charge on the spray nozzle is high enough, the surface tension of the fluid is exceeded and an aerosol 7 is produced. The spray nozzles are preferably elongated and tubular, and more preferably cylindrical, such as a capillary tube. A square, round or other cross section would be useful.

Downstream of the spray nozzles is a ring 22 having one or more discharge electrodes 24. In some applications favoring neutral droplets, the charge on the droplets is discharged to a chosen degree by means of the discharge electrode having an electrical charge the opposite polarity of the droplets. In a preferred mode, the droplets have a negative charge and the discharge electrode produces positive ions from the gas molecules near an ionization site. Ions are favorably produced near sharp points or edges of the discharge electrodes. The discharge electrodes are optional and may not be used when no discharge of the aerosol is desired. Some applications may require a partial discharge in which case, the position and the charge on the discharge electrode may be customized to provide partial discharge.

Downstream of the discharge electrodes is an optional ring 26 and one or more optional reference electrodes 28. In a preferred embodiment when the discharge electrodes are at a positive potential, the reference electrodes are at a potential that is negative with respect to that of the discharge electrodes 24 (which potential may preferably be ground potential). It is preferable to avoid having any positive ions migrate to the negative spray tip where they may interfere with the electric field around the Taylor cone. The purpose of these reference electrodes is to provide a bias (because of their potential and proximity) for the positive ions to be mildly attracted downstream toward the reference electrodes, particularly at start up of the device. After start up, the negative aerosol particles migrate downstream toward the discharge electrodes and preferentially attract the positive ions away from the spray tips 17.

Gas deflector 20 is shown as an annular frustoconical member completely around the spray nozzles 14. Typically the gas in these devices will be air, and we will refer to it throughout as air. However, in doing so, we intend to also include other gases that might be introduced into the device for any reason. For example, an inert gas atmosphere might be desirable for a reactive fluid. Multiple flow paths may be arranged (optionally using multiple flow deflectors) to shape the flow around the Taylor cone.

The gas or air deflector 20 may be of any shape that will assist in moving a gas along the desired path. Its purpose is to promote a first portion of the airflow 21 past the nozzles 14, the spray tips 17 and the Taylor cones 9 and to deflect a second portion of the airflow 8 away from the spray tips to later merge with the first portion downstream of the spray tips. Gas or air deflector 20 may have shaped walls to accomplish this. It may be completely around the nozzles or each individual nozzle for that matter or it may be only partially around the nozzles. It is sufficient that the air flow past the spray tip and the Taylor cone in a steady manner so as not to create disturbances on the Taylor cone and to make contact with the aerosol downstream of the spray tips to move some of the aerosol droplets away from the region around the spray tips. A cloud of charged aerosol has a negative effect on the stability of the Taylor cone and the airflow reduces the number of droplets in the region. In some cases, it may be possible to eliminate the air deflector 20 and use the walls of the device or other components in the device as the air deflector of the invention in directing the gas flow near the spray tips. In some cases, it may be desirable to promote the flow of all the air past the spray tips so the second portion of the airflow is minimal or zero.

As shown in FIG. 1, the deflector serves to direct a portion of the airflow 21 entering through holes 12 (or from another source) down over the spray tips and to direct another portion of the airflow 8 downward along the outside of the housing 10, or at least downward toward the exit but not along the nozzles or spray tips. The amount of airflow 21 directed past the spray tips (and the ratio of the airflow 21 to the airflow 8) can be controlled to an extent by altering the flow resistance of the airflow 21. This is controlled by altering the length of the deflector, the position of the air holes in the walls and/or the cross section of the flow area between the deflector and the nozzles or nozzle manifold or housing, for example.

The airflow past the spray tip can be near only one side of the tip or it can partially or fully around the spray tip. When an array of spray nozzles is used, the airflow may typically be around part or all of the periphery of all the spray nozzles or it may be around individual nozzles. A uniform airflow is preferred, however, both in time and in space. The flow should be sufficiently high to prevent the wicking and/or to transport some of the aerosol away from the region just downstream of the spray nozzle, but not so high as to disrupt the Taylor cone. Gentle laminar flow that produces few eddy currents or turbulence around the spray tip is preferred, though a fine and controlled turbulence may be useful in some situations. Preferably, the velocity of the airflow past the spray tip should be greater than the average velocity of the aerosol downstream of the spray tip, for example at one centimeter downstream from the spray tip.

In addition to preventing wicking and aiding aerosol transport, an airflow substantially completely around the aerosol also tends to shield or buffer the aerosol from other internal components of the device such as the discharge ring 22 and electrodes 24, reference ring 26 and electrodes 28 and angled wall/elbow 13. Even though the aerosol may flow past these components, the gas flow 21 tends to reduce the deposit by apparently buffering the aerosol from the surfaces. Moreover, the airflow 8 may also add to the sheath of air around the aerosol as it merges with airflow 21 downstream of the spray tips. Control of the ratio of the airflow 21 to the airflow 8 can further affect the sheathing of the aerosol and the subsequent deposit of aerosol on the internal components and the device wall.

Figure 3A:
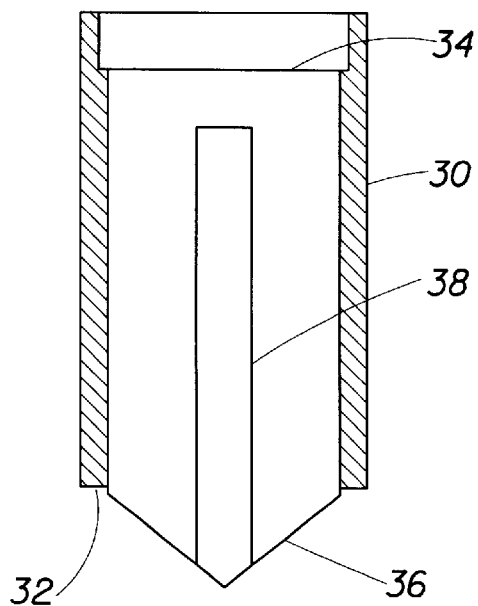
FIG. 3A shows an end view of the same spray tip.
Figure 3:
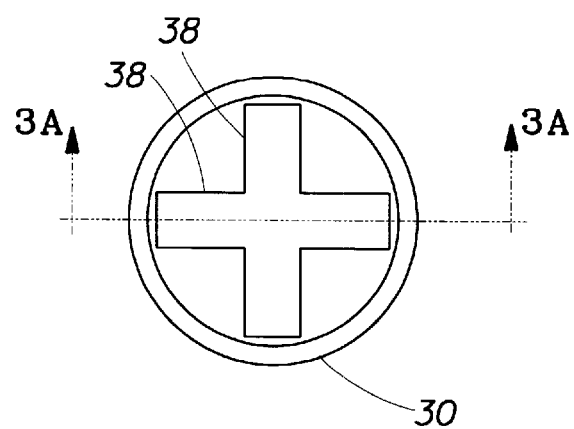
FIG. 3 shows the section view of a preferred EHD spray tip according to the invention.

One preferred spray nozzle design is shown in FIGS. 3 and 3A. Each spray nozzle 30 includes a round tube having a spray tip 32 at one end and a connection to the source of fluid to be aerosolized at the other end. The spray tip can be merely the end of the spray nozzle or can optionally include other designs or elements to promote better Taylor cones. In FIGS. 3 and 3A a partitioning plug 34 is secured in the spray nozzle at the spray tip. The partitioning plug 34 is a cylindrical element terminating in a cone 36 which becomes part of the spray tip for creation of the Taylor cone. The partitioning plug is machined to have four ribs 38 and having therefore a cross section in the shape of a cross to provide four paths for the fluid in the spray nozzle. This has been found to improve the formation of the Taylor cone and to increase the throughput of fluid. Other designs may result in one or more Taylor cones at each spray tip. Multiple nozzles in any useful arrangement may be used in the device.

If the device in FIG. 1 is used to deliver therapeutic aerosol to a user in contact with the exit 15, then one possible operation may be as follows. A negative charge is imposed on the spray nozzles 14 until a Taylor cone 9 is formed at the spray tip 17 and the fluid is aerosolized into a droplet cloud or aerosol 7 which may migrate downstream of the spray tips. Upon user inhalation, air may enter the openings 12 somewhere along the outer wall of the device, flow 21 through the air deflector 20 past a portion of the spray nozzles 14 past the spray tips 17 and the Taylor cone 9 and in contact with the aerosol cloud to help move the cloud downstream through the discharge ring 22 (where the aerosol may be discharged) and the reference ring 26. The aerosol may then also encounter and be buffered by a sheath of air 8 entering through the air holes and passing downward along the walls of the device past the elbow 13 to the exit 15 and the user. Again, the air/gas flow at 21 and 9 could be provided from any source of gas, such as a pressurized gas source.

Figures 4, 5:
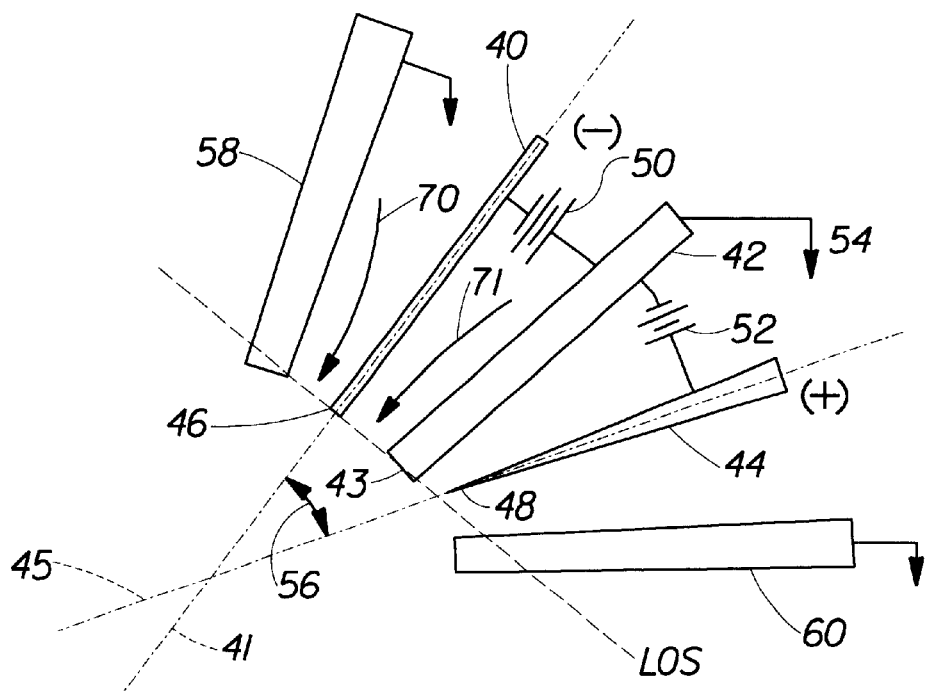
FIG. 4 is a schematic of important elements of an EHD sprayer including a discharge electrode for producing a corona wind.
FIG. 5 is a schematic of another embodiment of the invention for pulmonary delivery of drugs in a clinical setting where the source of fluid to be aerosolized is remote from the EHD device.

Without the inhalation of the user, the device of FIG. 1 would require another source of force to move the air 21 from upstream of the spray nozzles past the Taylor cone. Such force could come from a pressurized gas or bellows, for example, or some other direct source. Another preferred way of obtaining the gas flow 21 with or without user inhalation is by induction or entrainment using the principle of an injector (sometimes known as an ejector or eductor). A gas flow is provided downstream of and away from the spray nozzles causing an induced air flow 21 past the spray tip and Taylor cone. One particularly useful device for producing a gas flow downstream of the spray nozzles utilizes the principle of corona wind. A corona wind may be used to discharge the aerosol, move the aerosol toward a desired target and to induce the air flow 21 past the spray nozzles. Exemplary means for producing corona wind is shown in FIG. 4 and also in U.S. patent application Ser. No. 60/130,893 entitled "Directionally Controlled EHD Aerosol Sprayer", filed Apr. 23, 1999, and incorporated herein by reference.

FIG. 4 provides a schematic of an embodiment of the induced flow EHD aerosol sprayer. In this embodiment, the basic sprayer has a spray nozzle 40 having a spray tip 46 and central axis 41, a first reference electrode 42, and discharge electrode 44 having a central axis 45. A DC voltage source 50 electrically connects and maintains the spray nozzle 40 at a negative voltage with respect to reference electrode 42. A second DC voltage source 52 electrically connects and maintains the discharge electrode 44 at a positive voltage with respect to reference electrode 42. Ground 54 maintains reference electrode 42 at a ground reference voltage, approximately zero volts DC. It will be understood that the reference electrode 42 could be merely made of a dielectric material and in that case not be electrically charged at all. But if it is a conductor and is charged, it is conveniently at ground potential, but it could be at any potential that is negative with respect to the discharge electrode and positive with respect to the spray nozzle. Moreover, the polarity of the charge on the spray nozzle and discharge electrode are conveniently negative and positive respectively, but it is only necessary that the charges are negative and positive with respect to each other (and the reference electrode).

This embodiment also incorporates an optional second reference electrode 60 near the discharge electrode on the side opposite the first reference electrode 42 and an optional third reference electrode 58 near the spray nozzle on the side opposite the first reference electrode. Reference electrode 58 could again be merely dielectric, but is preferably a conductor and is at a potential which is positive with respect to the spray nozzle 40 and reference electrode 60 is at a potential which is negative with respect to the discharge electrode 44. Conveniently they are both at ground potential. Reference electrodes 58, 60 and spray nozzle 40 create air flow paths at 70 and 71 respectively. Air is induced at least partially by the corona discharge to move down the flow path 70 and 71 past the spray tip 46 and the Taylor cone to provide stability.

Spray nozzle 40 is typically a capillary tube or other tube, plate or any other shape used to deliver fluid in EHD applications. In some embodiments the tube used for spray nozzle 40 may have a plain spray tip 46 such as the end of the tube or one designed specifically for EHD spray applications (such as that shown in FIG. 3). These tips promote the formation and stability of the Taylor cone. The invention includes apparatus including a single spray nozzle that can produce multiple Taylor cones and apparatus with multiple spray nozzles. The device shown in FIG. 4, for example, can represent one spray nozzle or could represent a cross section of an elongated device having multiple spray electrodes or a planar spray electrode in a plane perpendicular to the paper. Multiple discharge electrodes and reference electrodes would also be within the scope of the invention, though each of the discharge electrodes and reference electrodes shown in FIG. 4 could be multiple electrodes within the same perpendicular plane or could also be elongated planar electrodes.

Discharge electrode 44 typically has a sharp discharge tip 48 or a knife-edge or other sharp points or other protrusions. As is known in the art, these sharp shapes tend to promote the formation of ionized air molecules. Alternatively, any tip shape that is capable of ionizing air molecules may be utilized. The discharge electrode is generally elongated and has a fairly easily definable central axis 45. Whether elongated or not, however, the tip 48 will have a geometry which allows significant ionization in the neighborhood of one or more sites on the discharge electrode and movement of the ions away from these sites in a direction which is predictable and reproducible. When the central axis is easily definable the direction of movement of the ions and ultimately the aerosol is generally parallel with this axis. When the axis is not easily definable, the direction of movement of the ions and the aerosol is predictable and reproducible away from the sites in a direction that we will define as axial to the discharge sites. Discharge electrodes with multiple ionization sites and multiple discharge electrodes (with or without multiple spray nozzles) are within the scope of the invention. In the case where a reference electrode is near the discharge electrode, the initial ion stream from the discharge electrode may by modified by the electric field between the discharge and the reference electrode. The movement of ions is then still predictable, but it influenced not only by the geometry of the discharge electrode, but also obviously any nearby electric fields.

The discharge electrode is located sufficiently close to the spray nozzle 40 and to the spray tip 46 and is oriented with respect thereto such that the ions from the discharge electrode may intercept the aerosol downstream of the spray tip 46. If the interception point is remote from the spray tip at a point where the aerosol has had sufficient time to become quite disperse, the effect of the ion cloud to move the aerosol in the desired direction and to induce air flow along the spray nozzle at 70 and 71 is diminished. Therefore, the discharge electrode is preferably located sufficiently close to the spray nozzle 40 and to the spray tip 46 and is oriented with respect thereto such that the ions from the discharge electrode may intercept the aerosol proximate the spray tip 46 before the aerosol has dispersed to any great degree.

The first reference electrode 42 is located between spray nozzle 40 and discharge electrode 44. This reference electrode can be a wire, screen, plate, tube or other shape which modifies the field between the spray nozzle and the discharge electrode. When used for influencing the flow of air near the spray nozzle and the Taylor cone, the reference electrode preferably has a shape and size sufficient for that purpose. In some embodiments, the spray end 43 of reference electrode 42 may be located proximate but not intersecting the line LOS that connects the spray tip 46 to discharge tip 48. In other embodiments, the spray end 43 of reference electrode 42 may be located to barely intersect the line LOS. In a preferred embodiment, however, the reference electrode 42 is positioned so that it crosses line LOS and the spray end 43 is past the line LOS but not substantially within the region of the aerosol spray downstream of the spray nozzle during use. With the reference electrode in this preferred position, the electric field generated between the spray nozzle 40 and reference electrode 42 is substantially de-coupled from the electric field generated between the discharge electrode 44 and reference electrode 42. Thus, changes in the relative position of the spray nozzle 40 with respect to reference electrode 42 or changes in the electric field strength generated between the spray nozzle 40 and reference electrode 42 have little, if any, impact on the electric field generated between the discharge electrode 44 and the reference electrode 42. Similarly, changes in the relative position of the discharge electrode 44 with respect to reference electrode 42 or changes in the electric field strength generated between the discharge electrode 44 and reference electrode 42 have little, if any, impact on the electric field generated between the spray nozzle 40 and the reference electrode 42.

However, the existence and the position of the reference electrode contribute with the discharge electrode to controlling the direction of the aerosol delivery. Without the reference electrode, the charged aerosol would tend to be attracted toward the tip of the discharge electrode. The positive ions from the tip of the discharge electrode would also be attracted toward the aerosol and the spray nozzle tip. The aerosol and the positive ions would then tend to meet substantially in between the spray nozzle and the discharge electrode. The reference electrode is positioned such that it reduces this tendency so that the aerosol and the positive ions intersect more near the intersection of their respective central axes downstream of the electrodes. In many applications, the discharge electrode is positioned such that the aerosol is moved generally in the direction of the positive ion flow and toward the desired target. In a pulmonary drug delivery application, the desired target would generally be the exit of the device which would interface the user's mouth.

The discharge electrode 44 and the reference electrodes 42, 58, 60 are fixed in the EHD device in such a manner and with respect to the spray nozzle 40 such that a source of gas may flow along a gas flow path such as at 70 and/or 71 alongside the spray nozzle. This air movement along the gas flow path 70 and/or 71 has been found to contribute to a very stable Taylor cone at the tip 46. The airflow also helps move the aerosol to the location where the positive ions from the discharge electrode impact the aerosol. The airflow along the path 70 and/or 71 appears to be at least partially induced by the corona wind from discharge electrode 44. Additionally, by controlling the amount of airflow at 70 and 71 (by upstream resistance, for example) and the amount of corona wind (by control of voltage or upstream resistance in the flow path, for example) one can somewhat alter the flow direction of the aerosol.

Preferably, reference electrode 42 and spray nozzle 40 are positioned such that the electric field intensity is largest between spray tip 46 and spray end 43, as for example when they are angled toward each other and the spray tip 46 and the spray end 43 are relatively closer together than other parts of the electrodes. This relative position of spray nozzle 40 and reference electrode 42 minimizes any tendency for the dispensed fluid to coat or collect on the outside of spray nozzle 40. It also has some positive effect on the induced air flow past at 70 and/or 71 due to the corona wind. Collection of fluid on the outside of spray nozzle 40 (with the spray nozzle fairly vertical and the nozzle tip at substantially the lowest point) is most likely when the spray nozzle 40 dispenses the aerosol in the upward direction and is least likely when the spray nozzle 40 dispenses the aerosol in the downward direction. Collection of fluid reduces the quantity of the fluid that is converted into an aerosol. Additionally, this fluid collection has the potential to disrupt or interfere with the Taylor cone. Any disruption or interference with this cone affects the aerosol droplet size and the droplet size distribution. This relative position of spray nozzle 40 and reference electrode 42 also minimizes the tendency for the aerosol to coat or collect on the reference electrode 42. Any collection of the aerosol on the reference electrode 42 reduces the quantity of aerosol delivered to the user from the EHD aerosol sprayer. The field strength between the reference electrode 58 and the spray nozzle 40 is also similarly greater near the spray tip 46.

For inducing the air flow past the spray tip, the movement of the corona wind is most beneficial away from the spray tip 46 such as when the central axis 45 of the discharge electrode is oriented parallel to the central axis 41 of the nozzle or at some acute angle. Of course, the corona wind must intercept the aerosol in some manner to affect the direction of the aerosol. When used to deliver therapeutic agents by inhalation, it is also desirable to hold the EHD device parallel with or above the user's mouth. This desire suggests that it would be more beneficial to shift the direction of the aerosol by up to 90 degrees so that it is delivered substantially horizontally to the user. Both of these desires may be accomplished by maintaining an angle 56 between the nozzle central axis 41 and the discharge electrode central axis 45 between about 0 and 90 degrees, more preferably between 0 and 60 degrees. The invention will continue to work at angles in excess of 90 degrees, but it will be understood that the aerosol will be redirected by the corona wind more in the general direction of the nozzle at these higher angles. Ultimately, at 180 degrees, the corona wind would be moving substantially parallel to the nozzle central axis and would potentially move the aerosol back to the nozzle. This would substantially defeat the purpose of the invention. The aerosol is most preferably directed by the discharge electrode toward the device exit and/or ultimately to the user contacting a mouthpiece near the exit.

The discharge electrode tip 48 may be located either upstream or downstream of the spray tip 46. As mentioned earlier, in this position upstream of and sufficiently close to the spray tip 46, the ions from the discharge electrode may intercept the aerosol proximate the spray tip 46 before the aerosol has dispersed to any great degree. By the term "upstream" of the spray tip 46, we mean that when the spray nozzle is in a vertical orientation, the discharge electrode tip is above a line drawn through the spray tip 46 perpendicular to the nozzle central axis 41. By the term "downstream" we mean that the discharge electrode tip would be below the perpendicular line under the above conditions.

Preferably, reference electrode 42 and discharge electrode 44 are positioned such that the electric field intensity is largest between spray end 43 and discharge tip 48. This relative position of discharge electrode 44 and reference electrode 42 minimizes the quantity of ionized air molecules that flow to the reference electrode 42. Thus, this configuration maximizes the number of ionized air molecules (corona wind) available to discharge the aerosol. Additionally, this configuration also tends to maximize the aerosol quantity that moves with the corona wind and the induced air flow past the Taylor cone.

DC voltage source 50 electrically connects spray nozzle 40 to reference electrode 42 and maintains spray nozzle 40 at a negative potential. DC voltage source 52 electrically connects discharge electrode 44 to reference electrode 42 and maintains discharge electrode 44 at a positive potential. A positive potential is preferred on the discharge electrode to form the corona wind discussed above. A negative voltage on the discharge electrode 44 would form an ion stream easier; however, these negative ions (electrons) have a very small mass. Thus, using electrons to discharge the aerosol has relatively little impact on the movement of the aerosol. Voltage sources 50 and 52 typically provide between one and twenty kilovolts, with the preferred voltage being between three and six kilovolts. The best voltage for aerosolizing a particular fluid depends on the fluid's properties, principally the conductivity/resistivity, viscosity, surface tension, and flow rate. Additionally, the relative positions of the spray nozzle 40, reference electrode 42, and discharge electrode 44 will typically have some influence on the best voltage(s) to be applied to the spray nozzle 40 and discharge electrode 44. Furthermore, the type of nozzle tip 46 and the aerosol droplet size will also influence the ideal voltage utilized in a particular application. The person of ordinary skill in the art of designing and using EHD sprayers is familiar with typical voltages utilized for specific fluids and equipment geometry. In some embodiments, the addition of a resistance in series with the voltage sources 50 and/or 52 may be required to prevent arcing between the spray nozzle 40 and reference electrode 42, or between reference electrode 42 and discharge electrode 44.

FIG. 5 is a schematic of another embodiment of the invention for pulmonary delivery of drugs in a clinical setting where the source of fluid to be aerosolized (and optionally the control system) is remote from the EHD device. An EHD sprayer is housed in a device 80 remote from the source of fluid. Fluid is introduced to the spray nozzle 88 at delivery tube 81. Auxiliary air 98 can be added through airway 82 in sequence to an inhalation cycle, for example. The device 80 interfaces to the patient through exit line 84 which may lead to a mouthpiece or face mask for the patient. The device 80 also includes a discharge electrode 90 and reference electrodes 91 and 92. A high potential field is maintained between the discharge electrode and the spray nozzle in the manner described above. Reference electrode 91 also has an applied potential intermediate the potential of the spray nozzle and the potential of the discharge electrode. Preferably, the discharge electrode is at a positive potential and the spray nozzle is at a negative potential for the reasons stated above. Preferably, both reference electrodes 91 and 92 are at ground potential for convenience. Multiple spray nozzles, discharge and reference electrodes are again within the scope of this embodiment.

A flow straightening plate 86 is fixed in the EHD device upstream of the electrodes. The flow straightening plate has holes 94 and 96 therethrough to pass gas past the discharge electrode and past the spray nozzle 88, the spray tip 89 and Taylor cone along paths 102 and 104 at the exit end of the spray nozzle. This flow at 102 and 104 stabilizes the Taylor cone at the spray tip 89 and helps transport aerosol away from the spray tip or tips. The holes 96 near the spray nozzle are preferably larger than the holes 94 away from the spray nozzle to promote greater air flow past the spray tip 89. The size of the holes can be altered to customize the flow past the spray tip in terms of location and velocity.

The corona wind 100 from the discharge electrode 90 also aids in inducing the flow 102 and 104 past the spray tip, particularly when the patient is not inhaling. With the force of a strong patient inhalation, auxiliary air 98 is induced through the flow straightener and past the spray tip. If the patient has a limited ability to inhale or if dosing is desired independent of the patient inhalation, then the corona wind provides the force for inducing the air flow 102 and 104 past the spray tip.

Figure 6:
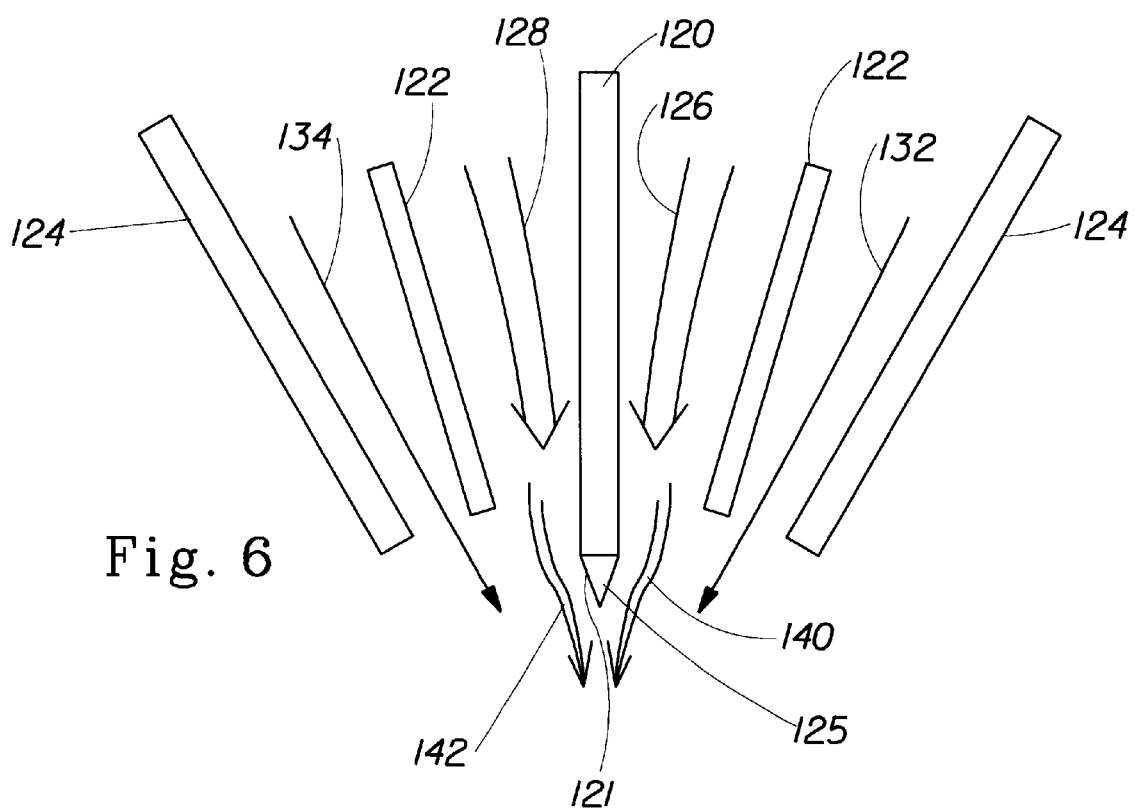
FIG. 6 is a schematic of another embodiment of the invention which utilizes multiple flow deflectors for shaping the airflow past the Taylor cone.

FIG. 6 shows the use of multiple flow deflectors for customizing the flow past the Taylor cone. A spray nozzle 120 is in communication with a source of fluid to be aerosolized. As described above, a Taylor cone 125 is formed at the end of the spray nozzle at the spray tip 121. First deflector 122 (which could completely surround the spray nozzle 120) is used with a source of gas to direct the flow 126 and 128 past the spray nozzle 120 and the spray tip 121. Second flow deflector 124 (which could completely surround the spray nozzle 120 and the first flow deflector 122) is used to direct a source of gas along paths 132 and 134 at an angle with respect to the flow 126 and 128. Because of the angular relationship, the flow 132, 234 tends to compress the flows 126, 128 more toward the spray tip and the Taylor cone 125 to more beneficially protect the Taylor cone and envelop the aerosol.

Figure 7:
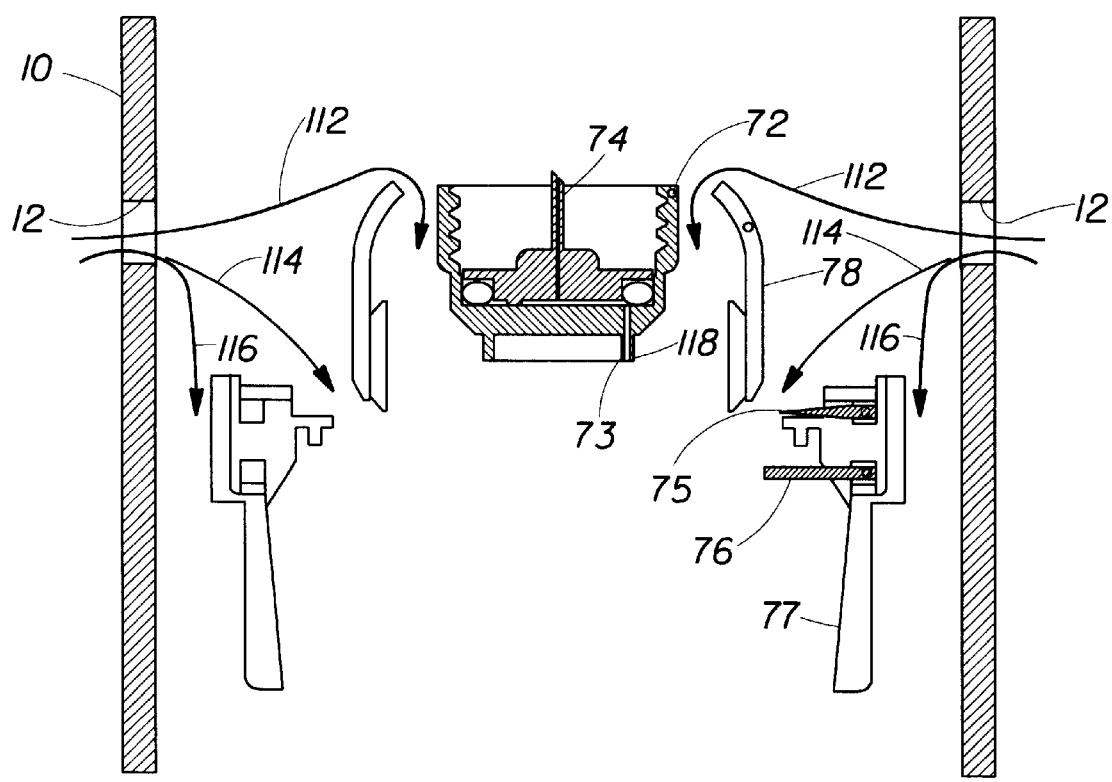
FIG. 7 is a breakaway section view of a portion of a device according to the invention including an alternative deflector/diffuser for further controlling the airflow past the Taylor cone.

FIG. 7 shows an alternative design for the flow deflector that is particularly useful when it is desirable to reduce the airflow past the spray nozzles to a very low velocity and flow rate. The EHD aerosolization takes place as in the device in FIG. 1. Fluid is delivered through a feed tube 74 to a nozzle block 72 and individual nozzles 73. An electric potential is placed on the nozzles which charges the fluid such that as the fluid emerges from the tip or end of the nozzles 73 a so-called Taylor cone is formed. This cone shape results from a balance of the forces of electric charge on the fluid and the fluid's own surface tension. Desirably, the charge on the fluid overcomes the surface tension and at the tip of the Taylor cone, a thin jet of fluid forms and subsequently and rapidly separates a short distance beyond the tip into an aerosol.

Downstream of the spray nozzles 73 is a holder 77 having one or more discharge electrodes 75 and one or more reference electrodes 76. In some applications favoring neutral droplets, the charge on the droplets is discharged to a chosen degree by means of the discharge electrode having an electrical charge the opposite polarity of the droplets. In a preferred mode, the droplets have a negative charge and the discharge electrode produces positive ions from the gas molecules near an ionization site. Some applications may require a partial discharge in which case, the position and the charge on the discharge electrode may be customized to provide partial discharge. In a preferred embodiment when the discharge electrodes 75 are at a positive potential, the reference electrodes 76 are at a potential that is negative with respect to that of the discharge electrodes (which potential may preferably be ground potential). It is preferable to avoid having any positive ions migrate to the negative spray tip where they may interfere with the electric field around the Taylor cone. The purpose of these reference electrodes is to provide a bias (because of their potential and proximity) for the positive ions to be mildly attracted downstream toward the reference electrodes, particularly at start up of the device. After start up, the negative aerosol particles migrate downstream toward the discharge electrodes and preferentially attract the positive ions away from the nozzles 73.

We have learned that in some designs the aerosol may have such an electrical attraction for the discharge electrodes before it breaks away from the nozzle spray tip, such that the Taylor cone itself may be biased from its normal downward appearance (as shown in FIG. 2) to an orientation to where its tip is actually pointing more toward its nearest discharge electrode such as shown at 118. If a high velocity airflow is moved past the nozzle, the benefits as recited above may be tempered by a shearing action on the outwardly facing Taylor cone 118. We have found that the airflow is necessary past the nozzle, its velocity should in these cases be reduced until the shearing is reduced.

This can be accomplished according to the invention by designing the flow deflector as a diffuser 78. The diffuser is a deflector that has a smaller cross section at the air entry point and a larger cross section downstream near the spray tip of the nozzle. Because of the expanding cross section, the velocity of the airflow decreases along its path. In operation, air enters through holes 12 in the walls of device 10. Depending on the flow resistance of the diffuser, a portion 112 of the air flows into the diffuser and past the nozzles and the Taylor cone. An additional portion of the air is deflected by the diffuser downwardly away from the nozzles outside of the diffuser. For example, a portion 114 of the air may flow between the diffuser and the holder 77 and a third portion 116 of the air may flow down the wall of the device. Of course, the direction of the additional air portions depends on the downstream design of the device. In a preferred embodiment as shown in FIG. 7, portions 114 and/or 116 may form a sheath of air around the aerosol as it moves through the device to protect the aerosol from being deposited on the internal components (including the discharge electrodes 75 and/or the reference electrodes 76) or the device walls.

Once again, the flow 112 past the nozzles can be controlled by the relative flow resistance for the airflow at 112 relative to the other flow paths. For example, the flow resistance for the flow 112 can be affected by the position and length of the diffuser, the cross section of the flow area between the diffuser and the nozzle block 72 and the position of the holes 12. As mentioned above, the velocity of the air past the spray tip is also affected by the increase in the cross section of the diffuser.

EXAMPLE

A series of experiments was performed to determine the fraction of sprayed liquid mass that was transported through an EHD spray device, without depositing on the device walls. The device consisted of an EHD sprayer mounted on a chamber containing a 45 degree bend, an inlet air around the spray nozzles, and an outlet. Holes were placed on the device walls such that they could be covered or uncovered to admit or not admit air through the walls. Measurements showed that when the air velocity around the spray nozzles was substantially less than the estimated average air velocity at about 1 cm downstream of the spray tips, the mass transfer efficiency was very low as most of the drops deposited on the device walls. When the air velocity was increased to greater than or equal to the average air velocity about 1 cm downstream of the spray tips, the mass transfer efficiency was high—typically over 80 per cent (of the fluid passed through the device). The efficiency could be varied by varying the amount of air admitted through the holes in the device walls.

We claim:

1. A high mass transfer electrohydrodynamic aerosol sprayer comprising:

a spray nozzle in fluid communication with a source of fluid to be aerosolized, the spray nozzle having at least one spray tip near which the fluid exits the spray nozzle, forms a Taylor cone and is aerosolized by electrohydrodynamic spraying;

a gas flow deflector for directing a gas past the spray tip and sweeping at least a portion of the aerosol away from the spray tip, and a first voltage source maintaining the spray nozzle at a negative potential.

2. The high mass transfer electrohydrodynamic aerosol sprayer of claim 1 wherein the spray nozzle is an elongated tube in fluid communication with a source of fluid at an upstream end thereof, the spray tip is located at a downstream end of the elongated tube and wherein the gas flow deflector directs the gas along at least a portion of the spray nozzle and past the spray tip.

3. The high mass transfer electrohydrodynamic aerosol sprayer of claim 2 wherein the gas flow deflector directs the gas along and substantially parallel to at least a portion of the spray nozzle and past the spray tip substantially completely around the spray nozzle.

4. The high mass transfer electrohydrodynamic aerosol sprayer of claim 3 wherein the gas flow deflector directs the gas in a laminar flow.

5. The high mass transfer electrohydrodynamic aerosol sprayer of claim 1 wherein the aerosol moves away from the spray tip at an aerosol velocity and the gas flow deflector directs the gas past the spray tip at a gas velocity greater than the average aerosol velocity one centimeter downstream of the spray tip.

6. The high mass transfer electrohydrodynamic aerosol sprayer of claim 5 wherein the gas flow deflector directs the gas in a laminar flow along at least a portion of the spray nozzle and past the spray tip substantially completely around the spray nozzle.

7. The high mass transfer electrohydrodynamic aerosol sprayer of claim 1 further comprising:

a discharge electrode; and a second voltage source maintaining the discharge electrode at a positive potential relative to the potential of the spray nozzle.

8. The high mass transfer electrohydrodynamic aerosol sprayer of claim 1 further comprising multiple spray nozzles.

9. A high mass transfer electrohydrodynamic aerosol sprayer comprising:

a spray nozzle in fluid communication with a source of fluid to be aerosolized, the spray nozzle having at least one spray tip near which the fluid exits the spray nozzle, forms a Taylor cone and is aerosolized by electrohydrodynamic spraying; and a gas flow deflector for separating a gas flow into at least two portions, for directing a first portion of the gas past the spray tip to sweep at least a portion of the aerosol downstream from the spray tip and for further directing the second portion of the gas away from the spray tip but thereafter into contact with the first portion of the gas and the aerosol downstream of the spray tip.

10. The high mass transfer electrohydrodynamic aerosol sprayer of claim 9 wherein the spray nozzle has a least one spray tip near which the fluid exits the spray nozzle, forms a Taylor cone which is elongated away from the spray tip in a preferred direction and is aerosolized by electrohydrodynamic spraying and wherein the gas flow deflector is further capable of directing the first portion of the gas past the spray tip substantially parallel to the preferred direction of the Taylor cone.

11. The high mass transfer electrohydrodynamic aerosol sprayer of claim 9 wherein the gas flow deflector directs the first portion of gas substantially completely around the spray nozzle.

12. The high mass transfer electrohydrodynamic aerosol sprayer of claim 11 wherein the gas flow deflector directs the second portion of gas substantially completely around the first portion of gas and the aerosol downstream of the spray tip.

13. The high mass transfer electrohydrodynamic aerosol sprayer of claim 9 which additionally includes a plurality of spray nozzles and a plurality of spray tips and wherein the gas flow deflector is capable of directing the first portion of gas substantially completely around the plurality of spray tips and of directing the second portion of gas substantially completely around the first portion of gas and the aerosol downstream of the spray tips.

14. The high mass transfer electrohydrodynamic aerosol sprayer of claim 9 wherein the gas flow deflector surrounds the spray tip and has an inlet end and an outlet end and wherein the deflector is designed such that the gas velocity is lower near the outlet end than near the inlet end.

15. The high mass transfer electrohydrodynamic aerosol sprayer of claim 14, wherein the cross sectional area available for the gas flow near the inlet end of the deflector is less than the cross sectional area near the outlet.

16. The high mass transfer electrohydrodynamic aerosol sprayer of claim 9 wherein the flow resistance of the gas flow deflector is such that the first portion of gas is smaller than the second portion of gas.

* * * * *